United States Patent [19]

Born et al.

[11] Patent Number: 5,132,031

[45] Date of Patent: Jul. 21, 1992

[54] COPPER DIHYDROCARBYL DITHIOPHOSPHYL DITHIOPHOSPHATES, THEIR PREPARATION AND THEIR USE AS ADDITIVES FOR LUBRICANTS

[75] Inventors: Maurice Born, Nanterre; Jean-Claude Hipeaux, Colombes; Valérie Maran, Rueil Malmaison; Armand Rossi, Montivilliers; Michel Thebault, Le Havre, all of France

[73] Assignee: Institut Francais Du Petrole, Rueil Malmaison, France

[21] Appl. No.: 570,613

[22] Filed: Aug. 21, 1990

[30] Foreign Application Priority Data

Aug. 21, 1989 [FR] France .................................. 8911153

[51] Int. Cl.$^5$ .......................................... C10M 137/06
[52] U.S. Cl. ........................ 252/32.700 E; 252/400.2; 252/389.2; 556/25
[58] Field of Search ............ 252/32.76 E, 46.4, 400.2, 252/389.2; 556/25

[56] References Cited

U.S. PATENT DOCUMENTS 4,766,228  8/1988  Born et al. ......................... 252/46.4
4,867,890  9/1989  Colclough et al. ............. 252/32.7 E
5,015,402  5/1991  Yodice et al. ....................... 252/46.4

Primary Examiner—Jacqueline Howard
Attorney, Agent, or Firm—Antonelli, Terry, Stout & Kraus

[57] ABSTRACT

Novel products of the copper dihydrocarbyl dithiophosphyl dithiophosphate type, their preparation and their use are described.

These products can be represented by the general formula:

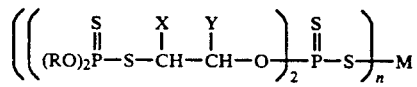

in which R particularly represents a substantially hydrocarbon monovalent radical with 1 to 30 carbon atoms, X and Y each represent a hydrogen atom or a substantially hydrocarbon monovalent radical with 1 to 30 carbon atoms, M represents copper in one of its two ordinary degrees of oxidation and n the degree of oxidation. The products according to the invention are usable as additives for lubricants in which they provide an effective protection against wear.

4 Claims, No Drawings

COPPER DIHYDROCARBYL DITHIOPHOSPHYL DITHIOPHOSPHATES, THEIR PREPARATION AND THEIR USE AS ADDITIVES FOR LUBRICANTS

The present invention relates to compounds of the copper dihydrocarbyl dithiophosphyl dithiophosphate type, more particularly used as antioxidant, antiwear, extreme-pressure and anticorrosive additives for lubricating oils, as well as to a process for the preparation of these compounds and the lubricants containing them.

Metallic dihydrocarbyl dithiophosphyl dithiophosphates and in particular those of zinc, cadmium, lead and antimony have already been described in U.S. Pat. No. 4,766,228. In the case of divalent metal salts, they are characterized by metal/P/S atomic proportions of approximately 1/6/12.

As a function of whether they are prepared from monovalent or divalent copper salts, the copper dihydrocarbyl dithiophosphyl dithiophosphates according to the invention are characterized by metal/P/S ratios of approximately 1/3/6 for monovalent copper or 1/6/12 for divalent copper. They can be represented by the general formula I:

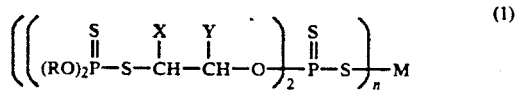

in which R represents a substantially hydrocarbon monovalent radical (or a mixture of substantially hydrocarbon monovalent radicals) with 1 to 30 carbon atoms. X and Y in each case represent a hydrogen atom or a substantially hydrocarbon monovalent radical with 1 to 30 carbon atoms and which can be linked to form a polymethylene chain. Thus, X and Y can each represent a hydrogen atom or a methyl, chloromethyl, chloroethyl, octyl or alkyl octanoate group, or together form a polyethylene chain with 4 $CH_2$ groups. M represents copper in one of its two ordinary degrees of oxidation, namely $Cu^{(n+)}$ and n the degree of oxidation or more specifically the equivalent of the anion of the $Cu^{(n+)}$ salt. The R radicals can be aliphatic, arylaliphatic, alicyclic aromatic or alkylaromatic and may optionally contain one or more atoms such as e.g. oxygen, nitrogen, sulphur, phosphorus or a halogen, etc.

The compounds according to the invention can be prepared by a process essentially comprising the following stages:

In a stage (a) a so-called "first generation" dithiophosphoric acid is prepared by reaction between a hydroxylated compound (substituted or unsubstituted alcohol or phenol) and phosphorus pentasulphide. The reaction can be represented by the following equation:

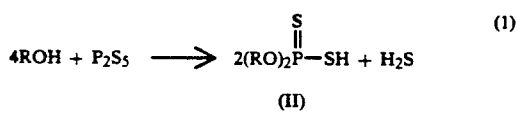

in which R is as defined as hereinbefore. Hydroxylated compounds which can be used are saturated or unsaturated aliphatic monoalcohols such as methanol, ethanol, propanols, butanols, pentanols, hexanols, heptanols, octanols, nonanols, etc.; mixtures of monoalcohols with a natural origin (e.g. fusel oil) or synthetic origin (e.g. alcohols resulting from the ALFOL process); alicyclic monoalcohols such as cyclohexanol; halides of aliphatic, alicyclic or aromaticaliphatic monoalcohols such as e.g. 2-chloroethanols and 2-bromoethanols, chloropropanols, bromopropanols, butanols, pentanols, etc.; chlorobenzyl, bromobenzyl, chlorophenylethyl or bromophenylethyl alcohols.

It is also possible to use (poly)oxyalkylenated monoalcohols, such as e.g. (poly)methoxy, propoxy, butoxy, phenoxy and alkylphenoxy ethanols and propanols, together with their halogenated derivatives; and aromatic hydroxylated compounds such as phenol and its substituted derivatves.

It is possible in this stage to use a mixture of two or more thus defined hydroxylated compounds. The reaction of the hydroxylated compound or compounds with the phosphorus pentasulphide is generally carried out as in the prior art, namely at temperatures between 20° and 180° C. and preferably between 50° and 150° C., the reagents being used in stoichiometric or near stoichiometric proportions.

In a second stage (b), the product (II) obtained in stage (a) is reacted with a compound having an epoxide function, such as ethylene, propylene, chloropropylene, butylene or cyclohexene oxide, or a fatty acid ester oxide and in particular alkyl (e.g. octyl) epoxy stearate. Preference is given to the use of ethylene and propylene oxides. The reaction can be represented by the following equation (2):

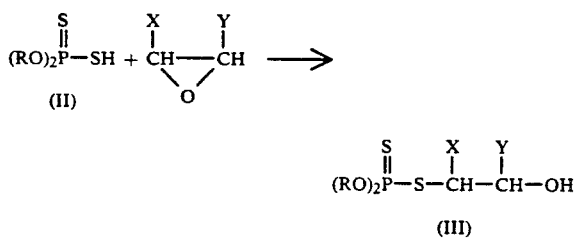

in which R, X and Y are as defined hereinbefore.

It is a $\beta$-hydroxyalkylation reaction of the compound of formula (II), giving rise to the hydroxylated compound of formula (III), which is a dithiophosphorus alcohol. This reaction is generally performed at temperatures between 0° and 150° and preferably between 20° and 130° C., the reagents being used in stoichiometric or near stoichiometric proportions.

In a third stage (c), the dithiophosphorus alcohol (III) is reacted with phosphorus pentasulphide, in accordance with a reaction diagram which can be represented by the following equation (3):

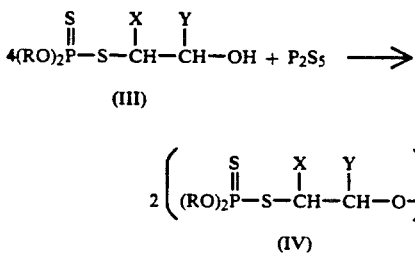

in which R, X and Y are as defined hereinbefore. This gives a so-called "second generation" dithiophosphyl dithiophosphoric acid (formula (IV)).

The reaction is carried out at temperatures generally between 20° and 120° and preferably between 40° and 90° C., the relative quantities of reagents being close to stoichiometry.

In a fourth stage (d), the dithiophosphoric acid (IV) is reacted in the form of an ammonium salt or an alkali metal salt with a copper salt having the desired degree of oxidation for the end product. The reaction can be represented by the following equation (4):

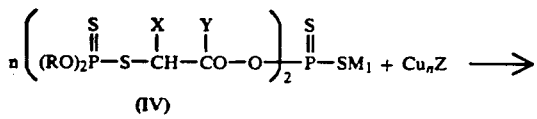
(IV)

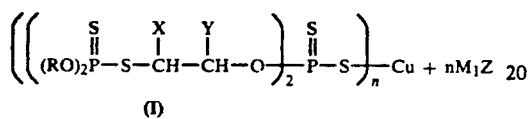
(I)

in which R, X, Y, M and n are as defined hereinbefore. $M_1$ is an alkaline metal or ammonium and n represents the anion equivalent of the salt $Cu^{(n+)}$. Thus, Z can be a hydrogen (chlorine or bromine) atom, a nitrate or carboxylate (acetate, formate) group or a carbonate, sulphate or similar half-group. Normally working takes place in an aqueous medium at temperatures between 0° and 100° and preferably between 40° and 60° C., the copper salt $Cu_n$ being used in excess.

According to a second synthesis method of the products according to the invention, it is possible to directly react the product (III) from stage (b) (dithiophosphorus alcohol) with phosphorus pentasulphide in the presence of oxide or hydroxide or copper carbonate in its desired degree of oxidation in order to give the sought copper dihydrocarbyl formula:

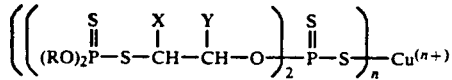

In this reaction hydrogen sulphide and water are also formed. The reaction is generally performed at between 40° and 100° and preferably between 60° and 90° C., in the presence of a solvent making it possible to eliminate the water formed, by azeotropic entrainment, the preferred solvent being cyclohexane.

The products according to the invention, which can be described as copper dihydrocarbyl dithiophosphyl dithiophosphates, can be advantageously used as additives for mineral and/or synthetic lubricants, particularly for protecting metal members against wear and corrosion, as well as for protecting lubricants against oxidation.

Based on the weight of the lubricant, said additives can be used at concentrations generally between 0.1 and 3% by weight and in proportions such that the copper to zinc atomic ratio is generally between 0.03 and 5 and preferably between 0.03 and 1.3. However, their main interest is in the antioxidizing synergism effect which they induce when associated with zinc dihydrocarbyl dithiophosphyl dithiophosphates, whose formula is:

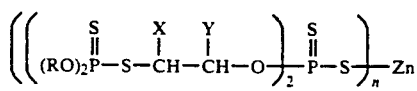

in which R represents at least one substantially hydrocarbon monovalent radical containing 1 to 30 carbon atoms; X and Y each represents a hydrogen atom or a substantially hydrocarbon radical with 1 to 30 carbon atoms and which can be linked to form a polymethylene chain, whilst n is the valency of the zinc.

This unexpected antioxidizing synergism effect makes it possible to formulate lubricating oils having very high antiwear and antioxidant properties for relatively low additive weight doses (0.5 to 2%).

In addition, the low metal content of these combinations of copper or zinc additives makes it possible to give a better protection to the catalytic containers equipping cars for equal performance levels with respect to conventional metallic dialkyl dithiophosphates (which have a much higher metal content and which are also used in doses between 0.8 and 2% by weight).

The weight concentration of the copper and zinc additives in the lubricating oil is, for the copper additive 0.1 to 0.5 and preferably 0.15 to 0.3% and for the zinc aditive 0.1 to 3 and preferably 0.7 to 1.2%.

The following examples illustrate the invention without in any way limiting the same.

EXAMPLE 1

Synthesis of a zinc dialkyldithiophosphyl dithiophosphate by the so-called "double decomposition" method.

Synthesis of a thiophosphorus alcohol from 4-methyl-2-pentanol

Into a 4 liter reactor equipped with a stirrer and which has been nitrogen purged are introduced 940.0 g (9.21 moles) of 4-methyl-2-pentanol and 444.4 g (2 moles) of $P_2S_5$. The formation temperature for the "first generation" acid is 85° to 90° C. Following the elimination of the dissolved $H_2S$ by bubbling a nitrogen flow, the dialkyldithiophosphoric acid obtained is transformed into thiophosphorus alcohol by the addition of 243.7 g (4.2 moles) of propylene oxide at between 30° and 35° C. The alcohol and propylene oxide excesses are eliminated by heating at 100° C. under reduced pressure.

1400 g of slightly viscous, very slightly coloured, clear thiophosphorus alcohol are collected having the following elementary analysis:

| C wt % | | H wt % | | S wt % | | P wt % | |
|---|---|---|---|---|---|---|---|
| Exp. | Theory | Exp. | Theory | Exp. | Theory | Exp. | Theory |
| 49.81 | 50.53 | 9.22 | 9.33 | 17.25 | 17.99 | 8.47 | 8.69 |

The IR and $^{13}C$ analyses confirm the expected chemical structure, namely:

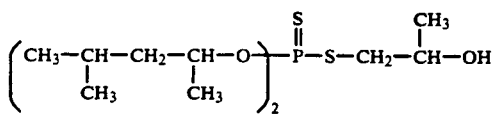

Into a second 1 liter reactor equipped with a stirrer and purged with nitrogen are introduced 150 g of the previously obtained thiophosphorus alcohol (0.42 mole), followed by heating to 95° C.

Using a powder introduction device, progressive addition takes place accompanied by stirring over a period of 2 hours of 22.2 g (0.10 mole) of P₂S₅, whilst keeping the temperature at about 95° C. This is followed by cooling, filtering under an inert atmosphere in the presence of diatomaceous earth and the recovery of 176 g of second generation acid (acidity = 1.2 10⁻³ acid equivalent/g).

This acid is neutralized with a 8.8 g soda solution in 200 cm³ of water. The milky solution obtained is extracted with 3 times 350 cm³ of hexane in order to eliminate the thiophosphorus alcohol excess and part of the sodium salt from the acid in partly soluble form.

The (lower) aqueous solution containing the purified sodium salt is treated for 3 hours, accompanied by stirring, using a solution of 45.5 g of zinc sulphate heptahydrate ZnSO₄, 7H₂O (0.158 mole) in 100 cm³ of water.

The milky suspension obtained is extracted with three times 200 cm³ of cyclohexane. The combined cyclohexane extracts are washed with water, dried on anhydrous sodium sulphate, filtered on diatomaceous earth and then evaporated at 100° C. under reduced pressure to constant weight.

This leads to the recovery of 105 g of highly viscous, translucent organic product, whose elementary analysis (Table 1) and ¹³C, ¹H NMR analyses confirm the structure. It is also confirmed by the infrared analysis indicating the characteristic absorption bands of zinc dialkyl dithiophosphates, particularly at 970 cm⁻¹ (which can be attributed to the P-O-C groups from the secondary alcohols), at 665 cm⁻¹ (which can be attributed to the P=S groups) and 545 cm⁻¹ (which can be attributed to the P-S groups). These absorption bands are much more intense than those of the corresponding conventional di-sec-butyl zinc dithiophosphate and in particular for the P=S and P-S bands. The product obtained corresponds to the following formula:

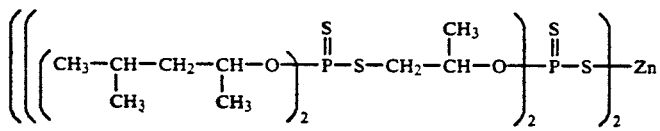

EXAMPLE 2

Synthesis of a zinc dialkyl dithiophosphyl dithiophosphate by the metal oxide method.

Into a 1 liter reactor, equipped with a DEAN-STARK separator system with a condenser and a powder reagent admission system, are introduced 150 g (0.42 mole) of thiophosphorus alcohol prepared in example 1, 300 cm³ of cyclohexane and 12.2 g (0.15 mole) of ZnO. The suspension obtained is heated, accompanied by stirring, up to cyclohexane reflux, the temperature of the medium being between 85° and 90° C.

By means of the powder reagent introduction system, over a 3 hour period progressive introduction takes place of 22.2 g (0.1 mole) of P₂S₅, the reaction water being heteroazeotropically entrained from the solvent.

After 7 additional hours of reflux, filtering the mixture and evaporating the solvent under reduced pressure, 165 g of a very slightly coloured, viscous, clear product are recovered, whose structure is confirmed by elementary analysis (table 1) and ¹H, ¹³C, ³¹P NMR analyses.

EXAMPLE 3

Synthesis of divalent copper dialkyl dithiophosphyl dithiophosphate by the so-called "double decomposition" method.

The experiment of example 1 is repeated, but the zinc sulphate is substituted by the same molar quantity of dihydrated divalent copper chloride CuCl₂,2H₂O (0.158 mole), i.e. 26.9 g.

Following reaction and then treatments, 148 g of a viscous, very dark green, but still clear product are recovered. The elementary analysis (table 1), the ¹H, ¹³C NMR and infrared analyses confirm the assumed structure, namely:

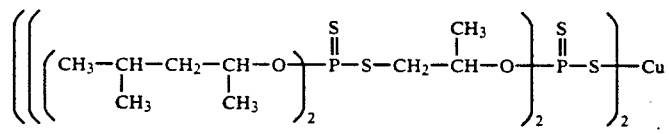

EXAMPLE 4

Synthesis of a divalent copper dialkyl dithiophosphyl dithiophosphate by the metal oxide method.

The experiment of example 2 is repeated whilst reacting, under the same synthesis conditions, 150 g (0.42 mole) of thiophosphorus alcohol prepared in example 1, 11.9 g of CuO (0.5 mole) and 22.2 g (0.1 mole) of P₂S₅ in 300 cm³ of cyclohexane.

This gives 154 g of product, whose elementary analysis (table 1) and ¹H, ¹³C NMR and infrared analyses are very close to those of the additive obtained in example 3 and which confirm the assumed structure.

EXAMPLE 5

Synthesis of divalent copper dialkyl dithiophosphyl dithiophosphate from divalent copper salts other than oxide.

The experiment of example 4 is repeated whilst substituting the CuO (0.15 mole) by 12.2 g of copper carbonate (constituted by an equimolar mixture of CuCO₃ and Cu(OH)₂).

As for the product of example 3, the analyses of the product obtained confirm the sought chemical structure.

EXAMPLE 6

Synthesis of divalent copper and zinc complex dialkyl dithiophosphyl dithiophosphate.

The experiment of example 2 is repeated, reacting 150 g of the thiophosphoric alcohol of example 1 with 22.2 g of $P_2S_5$ and a mixture of metal oxides constituted by 2.19 g of CuO (0.0275 mole) and 8.96 g of ZnO (0.11 mole), i.e. as Zn/Cu atomic ratio of 4.

After 10 hours heteroazeotropic entrainment with cyclohexane, filtration and evaporation, 158 g of a viscous, dark green, but clear product are recovered, whose analyses confirm the sought chemical structure (table 1).

EXAMPLE 7

Synthesis of a monovalent copper dialkyl dithiophosphyl dithiophosphate.

The experiment of example 4 is repeated, substituting the divalent copper contained in 11.9 g of CuO by a 50% reduced molar quantity of $Cu_2O$ (0.075 mole = 10.73), namely by a corresponding mass of identical metal.

The analyses confirm the assumed chemical structure of the product obtained (table 1), namely:

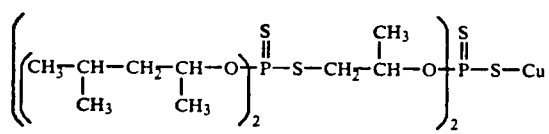

EXAMPLE 8

Synthesis of a monovalent copper and divalent copper complex dialkyl dithiophosphyl dithiophosphate.

The experiment of example 7 is repeated reacting under the same synthesis conditions 150 g (0.42 mole) of thiophosphoric alcohol, 22.2 g of $P_2S_5$ and a mixture constituted by 5.97 g of CuO (0.075 mole) and 5.38 g of $Cu_2O$ (0.0375 mole), i.e. a $Cu^{++}/Cu^+$ atomic ratio of 1.

After reaction and treatment, 154 g of product are collected, whose analyses confirm the sought structure (table 1).

After 10 hours of heteroazeotropic entrainment with cyclohexane, filtration and evaporation 157 g of a viscous, dark green, but clear product are collected, whose analyses confirm the sought chemical structure (table 1).

EVALUATION OF THE ANTIOXIDANT PROPERTIES OF THE ADDITIVES ACCORDING TO THE INVENTION

The antioxidant properties of the additives according to the invention and the antioxidizing synergism effect obtained by associating in a same lubricant formula zinc and copper dialkyl dithiophosphyl dithiophosphates were demonstrated by means of the TFOUT test (Thin Film Oxygen Uptake Test) making it possible to determine the oxidation stability of oils for petrol engines by thin film oxygen absorption.

This test performed at 160° C. makes use of an oxygen-pressurized cylinder, as well as a metal catalyst, a fuel catalyst and water simulating the conditions to which the oil can be exposed in a petrol engine. This test method can be used for engine oils with a viscosity between 3.8 and 26.1 $mm^2/s$ at 100° C., including reclaimed oils.

The experiments were carried out with a 200 NEUTRAL solvent mineral base oil containing a commercial set of detergent-dispersant additives and improving the viscosity index in the following proportions:
Detergent-dispersant set: 10% by weight
Viscosity index improving additive: 5% by weight Table 2 indicates the oxidation delays of said lubricant mixture observed in the presence of additives according to the invention, used either singly or in combined form. It can be seen that the combined use of the zinc and copper dialkyl dithiophosphyl dithiophosphates according to the invention gives a higher lubricant oxidation resistance than that which could have been expected by forming the algebraic sum of the antioxidant effects of each additive used alone, so that there is a significant antioxidant synergism effect between these two additive types.

TABLE 1

| Additive of example | Cation M m+ | ELEMENTS wt % | | | | | | | | | | Metal/P/S in atoms | |
|---|---|---|---|---|---|---|---|---|---|---|---|---|---|
| | | Theory | | | | | Found | | | | | | |
| | | C | H | S | P | Metal | C | H | S | P | Metal | Theory | Found |
| 1 | Zn ++ | 43.16 | 7.24 | 23.05 | 11.13 | 3.91 | 44.01 | 7.92 | 22.75 | 11.06 | 4.01 | 1/6/12 | 1/6.1/11.6 |
| 2 | Zn ++ | 43.16 | 7.24 | 23.05 | 11.13 | 3.91 | 44.42 | 8.05 | 22.94 | 10.94 | 4.05 | | 1/5.7/11.5 |
| 3 | Cu ++ | 43.21 | 7.25 | 23.07 | 11.14 | 3.81 | 44.35 | 7.88 | 21.72 | 10.48 | 3.68 | | 1/5.8/11.7 |
| 4 | Cu ++ | 43.21 | 7.25 | 23.07 | 11.14 | 3.81 | 44.49 | 8.11 | 21.89 | 10.28 | 3.58 | | 1/6.0/12.4 |
| 5 | Cu ++ | 43.21 | 7.25 | 23.07 | 11.14 | 3.81 | 44.25 | 8.12 | 21.09 | 9.98 | 3.71 | | 1/5.5/11.3 |
| 6 | Zn ++ | 43.17 | 7.24 | 23.84 | 11.13 | 3.13 | 43.89 | 8.17 | 19.80 | 9.39 | 2.60 | | 1/5.8/11.8 |
|   | Cu ++ |       |      |       |       | 0.76 |       |      |       |      | 0.80 | | |
| 7 | Cu + | 41.62 | 6.99 | 22.23 | 10.73 | 7.34 | 42.55 | 7.43 | 21.74 | 11.01 | 7.51 | 1/3/6 | 1/3.0/5.7 |
| 8 | Cu ++ | 42.67 | 7.16 | 22.78 | 11.00 | 5.02 | 43.39 | 7.51 | 20.93 | 10.44 | 5.31 | 1/4.5/9 | 1/4.0/8.6 |
|   | Cu + |       |      |       |       |      |       |      |       |      |      | | |
| 9 | Zn ++ | 42.64 | 7.16 | 22.77 | 10.99 | 2.58 | 43.52 | 7.48 | 21.10 | 10.47 | 2.41 | 1/4.5/9 | 1/4.6/8.7 |
|   | Cu + |       |      |       |       | 2.51 |       |      |       |      | 2.30 | | |

EXAMPLE 9

Synthesis of a monovalent copper and zinc complex dialkyl dithiophosphyl dithiophosphate.

The experiment of example 6 is repeated reacting 150 g of the thiophosphoric alcohol of example 1 with 22.2 g of $P_2S_5$ and a mixture of metal oxides constituted by 6.1 g of ZnO (0.075 mole) and 5.34 g of $Cu_2O$ (0.0375 mole), i.e. of Zn/Cu atomic ratio of 1.

TABLE 2

| Additive of Ex. 1 DTPDTP Zn (wt %) | Additive of Ex. 3 DTPDTP Cu(++) (wt %) | Lubricant oxidation delay (min) |
|---|---|---|
| 0.10 | — | 55 |
| 0.15 | — | 63 |
| 0.30 | — | 75 |

TABLE 2-continued

| Additive of Ex. 1 DTPDTP Zn (wt %) | Additive of Ex. 3 DTPDTP Cu(++) (wt %) | Lubricant oxidation delay (min) |
|---|---|---|
| 0.50 | — | 82 |
| 1.00 | — | 98 |
| 1.20 | — | 112 |
| 1.50 | — | 123 |
| — | 0.10 | 48 |
| — | 0.15 | 59 |
| — | 0.30 | 72 |
| — | 0.50 | 95 |
| 1.20 | 0.15 | 230 |
| 1.20 | 0.30 | 257 |

We claim:

1. A lubricating composition having anti-wear and antioxidant properties comprising a synthetic or a mineral lubricating oil component and an additive component comprising a mixture of at least one copper dihydrocarbyl dithiophosphyl dithiophosphate represented by the general formula:

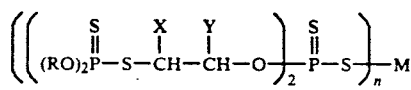

wherein R represents at least one hydrocarbon monovalent radical containing 1 to 30 carbon atoms, X and Y each represent a hydrogen atom or a hydrocarbon monovalent radical with 1 to 30 carbon atoms and which may be linked to form a polymethylene chain, M represents copper in one of its two degrees of oxidation and n represents the degree of oxidation and at least one zinc dihydrocarbyl dithiophosphyl dithiophosphate represented by the general formula:

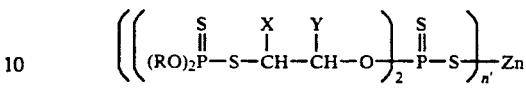

wherein R, X and Y are as heretofore defined and n' is the valency of zinc.

2. A lubricating composition according to claim 1, wherein the weight ratio of the copper dihydrocarbyl dithiophosphyl dithiophosphate to zinc dihydrocarbyl dithiophosphyl dithiophosphate in the lubricating oil is between 0.03 and 5.

3. A lubricating oil according to claim 2, wherein the weight concentration of the additive component mixture in the lubricating oil is between 0.2 and 3.5%.

4. A lubricating composition according to claim 1, wherein R represents at least one hydrocarbon radical selected from the group consisting of aliphatic, arylaliphatic, alycyclic aromatic and alkyl aromatic radicals and wherein X and Y represent a hydrogen atom, a methyl, chloromethyl, chloroethyl, octy or alkyl octanate group or together form a polymethylene chain having 4 CH₂ groups.

* * * * *